US008901519B2

(12) United States Patent
Schardt et al.

(10) Patent No.: US 8,901,519 B2
(45) Date of Patent: Dec. 2, 2014

(54) QUICK REGULATION OF THE RANGE OF HIGH-ENERGY ION BEAMS FOR PRECISION IRRADIATION OF MOVING TARGET VOLUMES

(75) Inventors: Dieter Schardt, Darmstadt (DE); Christoph Bert, Aschaffenburg (DE); Nami Saito, Darmstadt (DE); Bernhard Franczak, Darmstadt (DE); Chaudhri Naved, Darmstadt (DE); Pleskac Radek, Darmstadt (DE)

(73) Assignee: GSI Helmholtzzentrum für Schwerionenforschung GmbH, Darmstadt (DE)

( * ) Notice: Subject to any disclaimer, the term of this patent is extended or adjusted under 35 U.S.C. 154(b) by 1319 days.

(21) Appl. No.: 12/674,775

(22) PCT Filed: Jul. 22, 2008

(86) PCT No.: PCT/EP2008/005984

§ 371 (c)(1),
(2), (4) Date: Jan. 7, 2011

(87) PCT Pub. No.: WO2009/026997

PCT Pub. Date: Mar. 5, 2009

(65) Prior Publication Data

US 2011/0105821 A1 May 5, 2011

(30) Foreign Application Priority Data

Aug. 24, 2007 (DE) .................. 10 2007 040 299
Nov. 15, 2007 (DE) .................. 10 2007 054 919

(51) Int. Cl.
*G21K 5/02* (2006.01)
*G21K 5/10* (2006.01)
*A61N 5/10* (2006.01)
*G21K 5/04* (2006.01)

(52) U.S. Cl.
CPC ............... *G21K 5/04* (2013.01); *A61N 5/1043* (2013.01); *A61N 5/1049* (2013.01); *A61N*

(Continued)

(58) Field of Classification Search
USPC ............ 250/396 R, 397, 398, 491.1, 492.22, 250/492.23, 492.3; 378/16–20, 64, 65, 378/68–70, 145, 158, 205, 210
See application file for complete search history.

(56) References Cited

U.S. PATENT DOCUMENTS 5,117,829 A * 6/1992 Miller et al. .................. 600/427
5,151,605 A * 9/1992 Politiek et al. ............. 250/492.2

(Continued)

FOREIGN PATENT DOCUMENTS

DE       100 31 074 A1    1/2002
DE       103 23 654 A1    12/2004

(Continued)

OTHER PUBLICATIONS

Sven Oliver Grozinger, et al. Title: Simulations to design an online motion compensation system for scanned particle beams Phys. Med. Biol. 51 (2006) 3517-3531 XP020095856.

*Primary Examiner* — Bernard E Souw
(74) *Attorney, Agent, or Firm* — Reising Ethington PC

(57) ABSTRACT

The invention concerns a device and a process for adjusting the range of an ion beam, in particular for irradiation in tumor therapy. For this purpose, first the reference position of a target volume to be irradiated is determined. Subsequently, the range of an ion beam is configured such that said beam is adjusted to the reference position of the target volume, in such a manner that the Bragg peak, i.e. the maximal energy loss and thereby the maximal damage occurs in the region of the target volume which is to be destroyed. In the case that it has been determined that the reference position has been altered by a movement of the target volume, the ion beam is then deflected from the beam axis such that the ion beam is directed to various regions of a range modulator, in order that the ion beam experience a correspondingly adjusted energy loss in passing through the range modulator. This energy loss is adjusted to correspond to the change in position of the target volume in such a manner that the change in position is compensated for by the adjustment of the range of the ion beam, and the Bragg peak is returned to the region within the target volume.

21 Claims, 6 Drawing Sheets

(52) U.S. Cl.
CPC  5/1067 (2013.01); *A61N 2005/1087* (2013.01)
USPC ............... 250/492.22; 250/491.1; 250/396 R;
250/397; 378/70; 378/65; 378/68; 378/158;
378/205

(56) References Cited

U.S. PATENT DOCUMENTS 6,219,403 B1 * 4/2001 Nishihara ....................... 378/65
6,998,625 B1 * 2/2006 McKenna et al. ......... 250/492.21
2006/0193435 A1 * 8/2006 Hara et al. ..................... 378/65

FOREIGN PATENT DOCUMENTS

| DE | 10 2005 053 971 A1 | 5/2007 |
| JP | 2005296162 A | 10/2005 |
| JP | 2006 341010 A | 12/2006 |
| WO | WO 2005/110495 | 11/2005 |

* cited by examiner

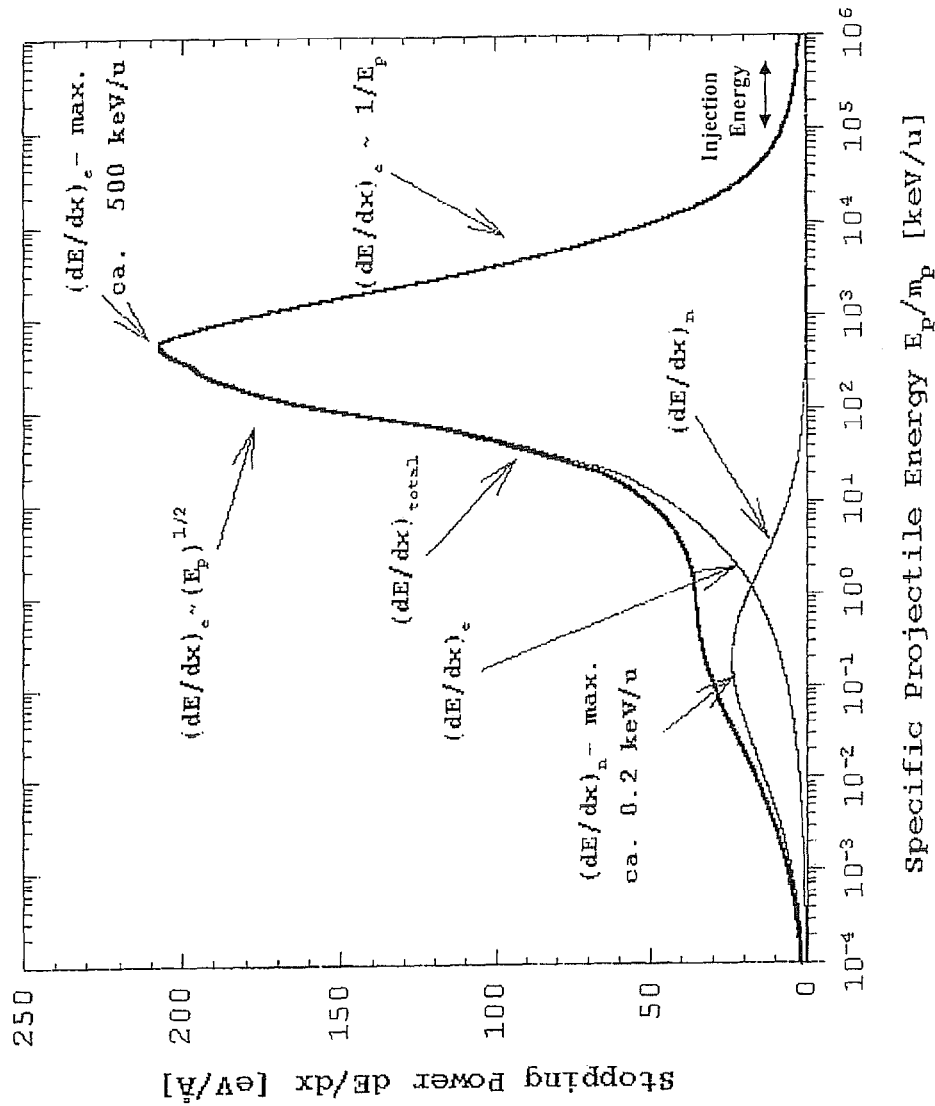
Fig. 1.a

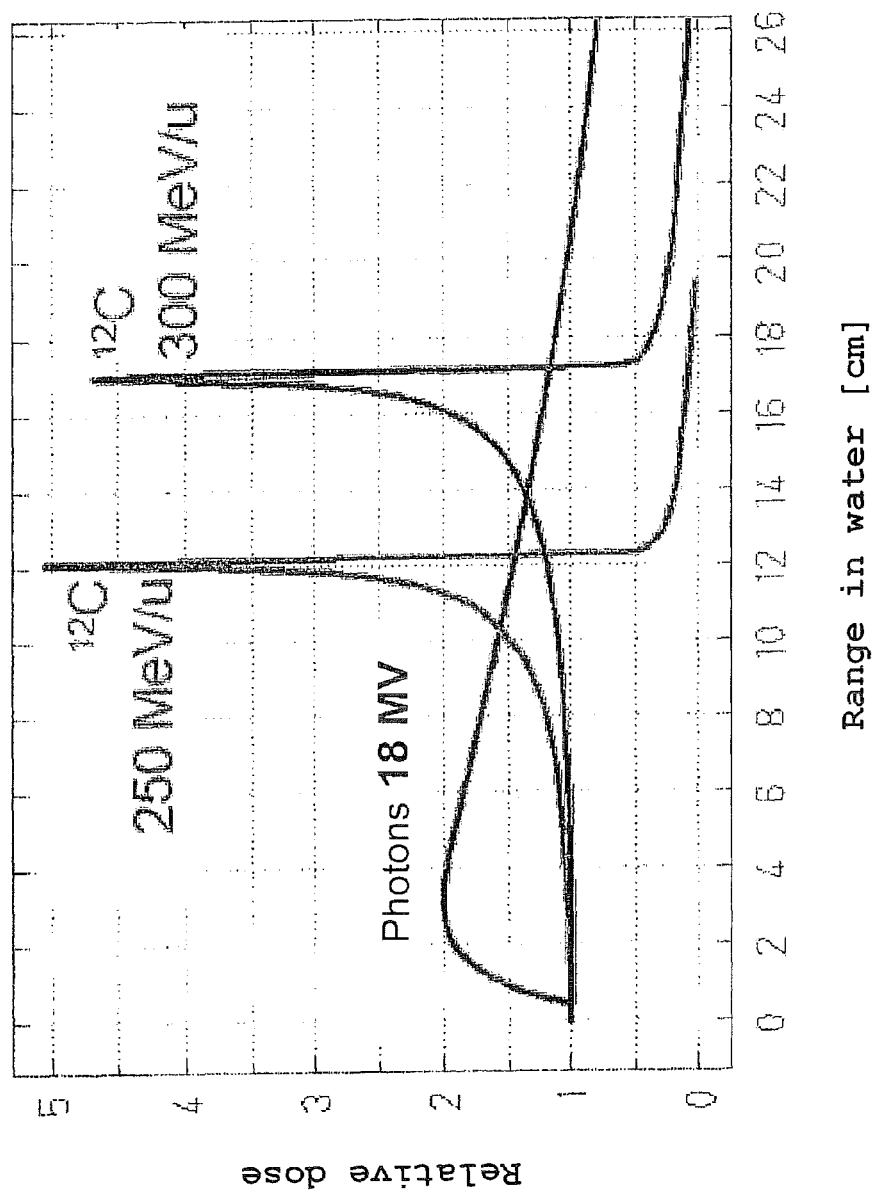
Fig. 1.b

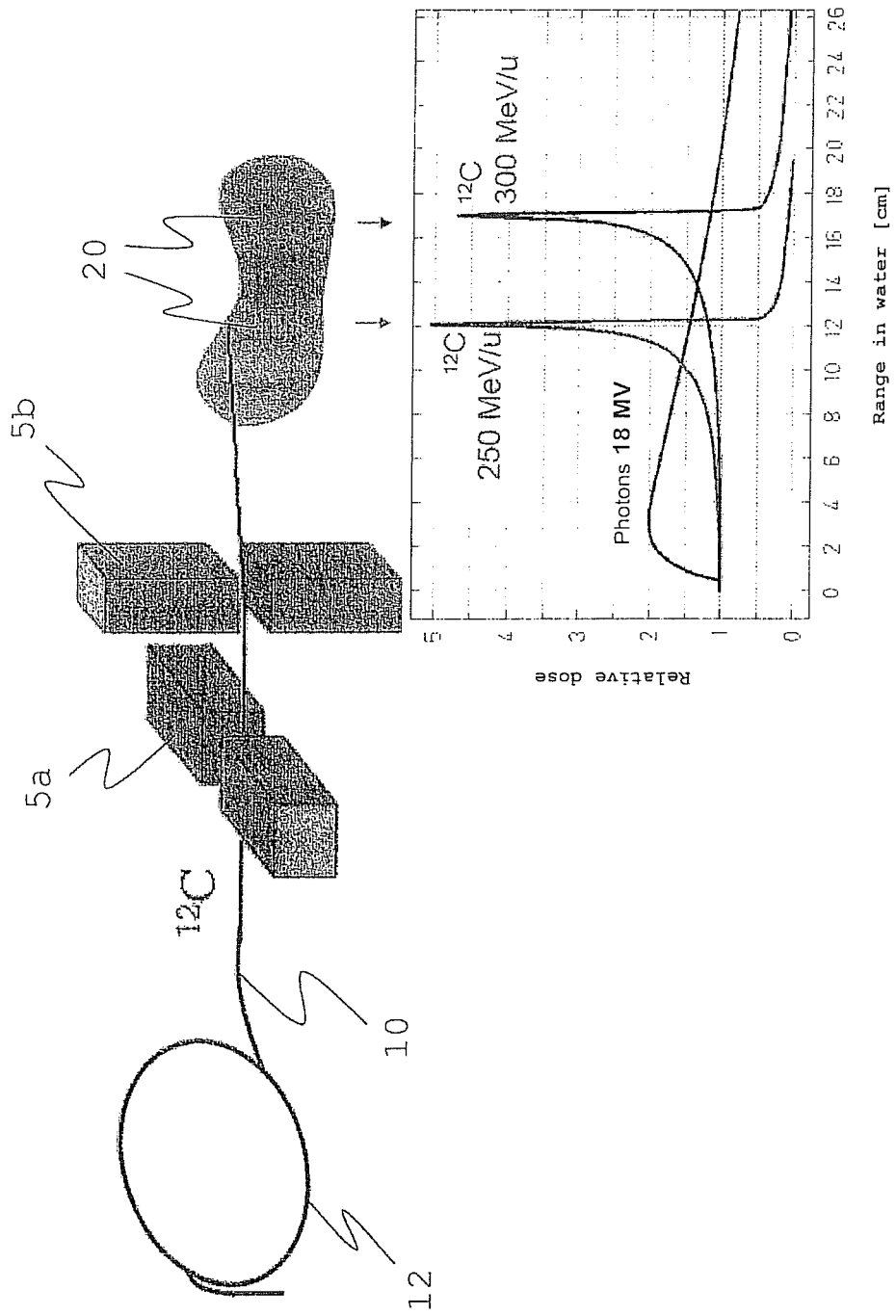
Fig. 2.a

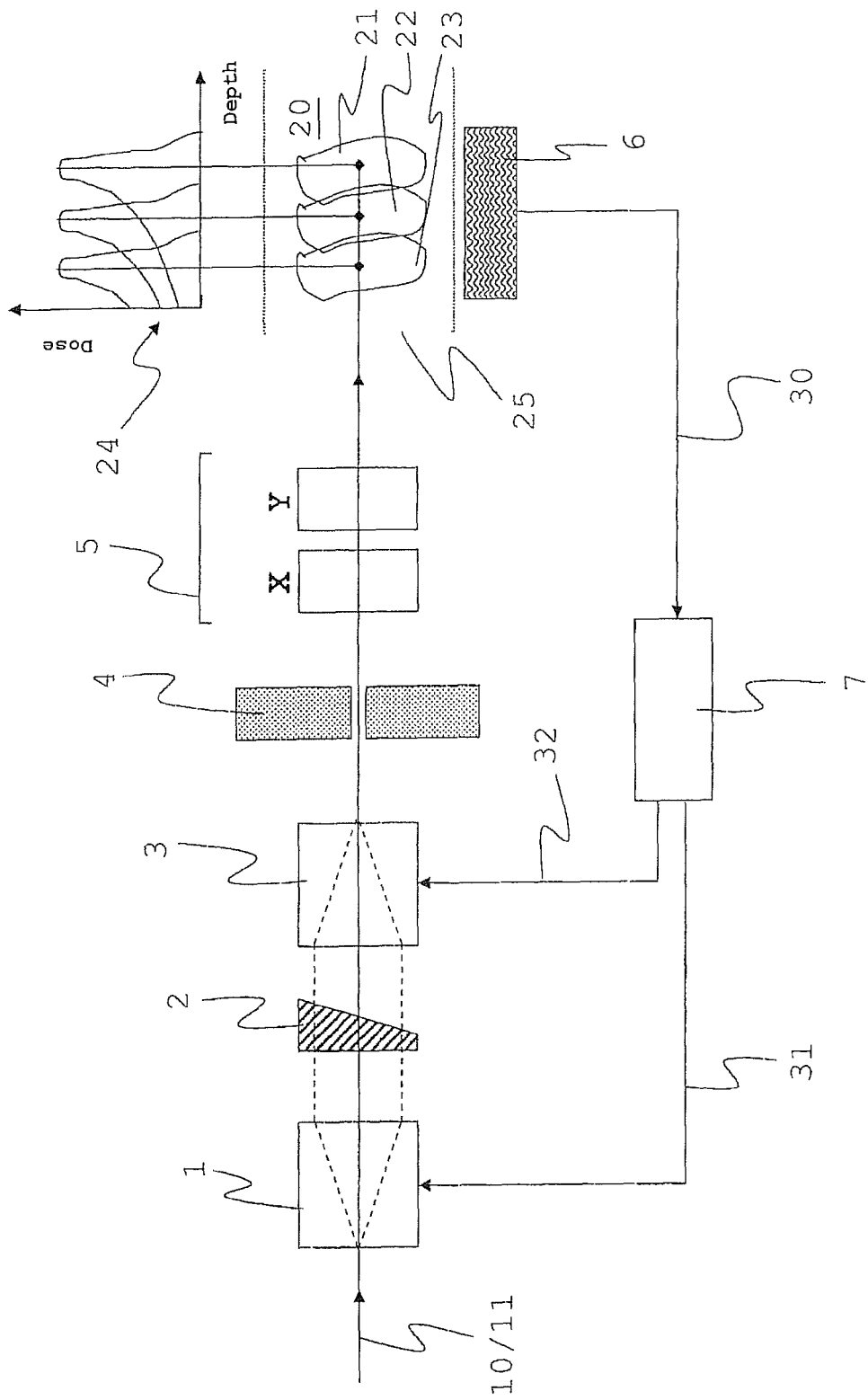
Fig. 2.b

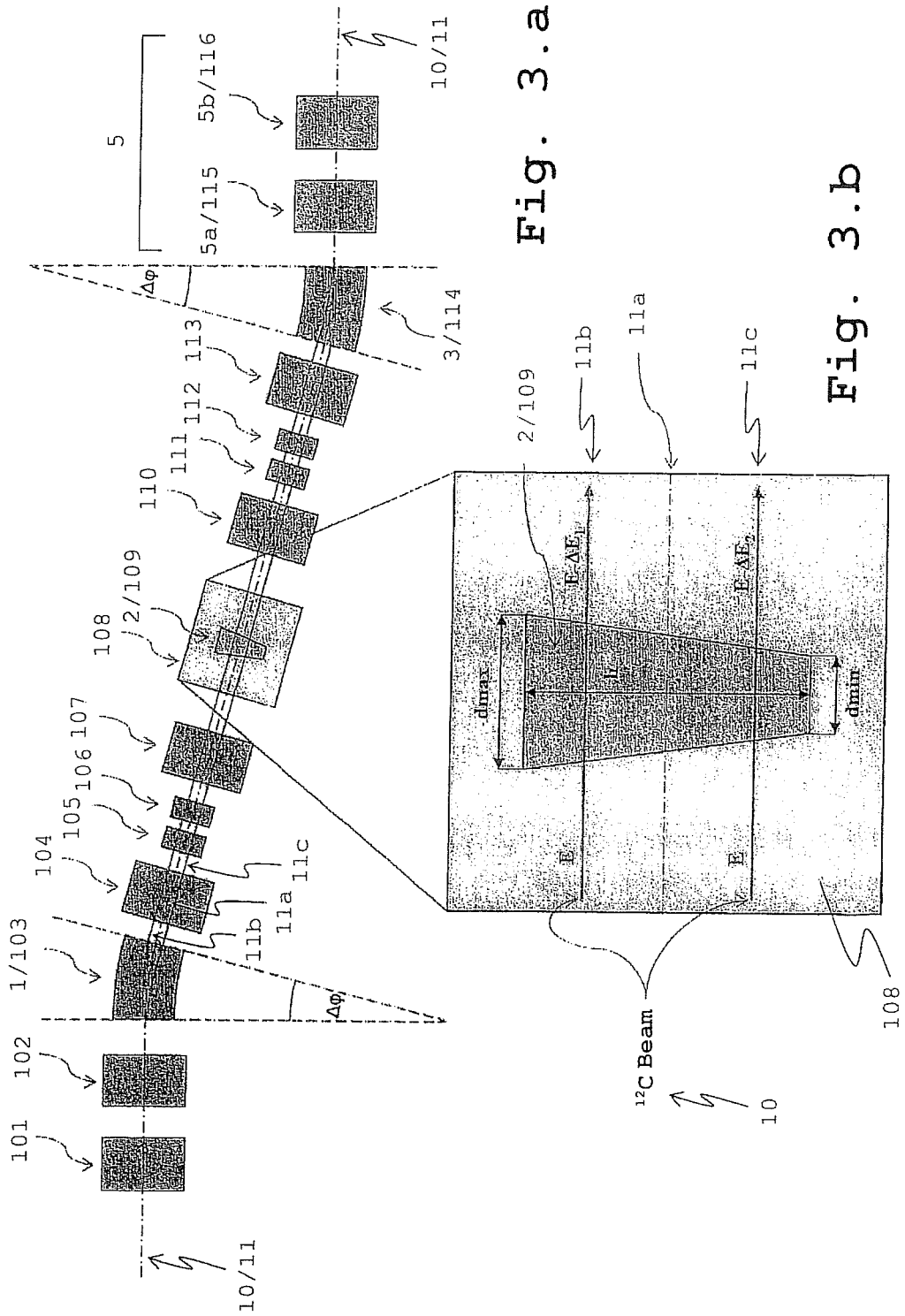
Fig. 3.a
Fig. 3.b

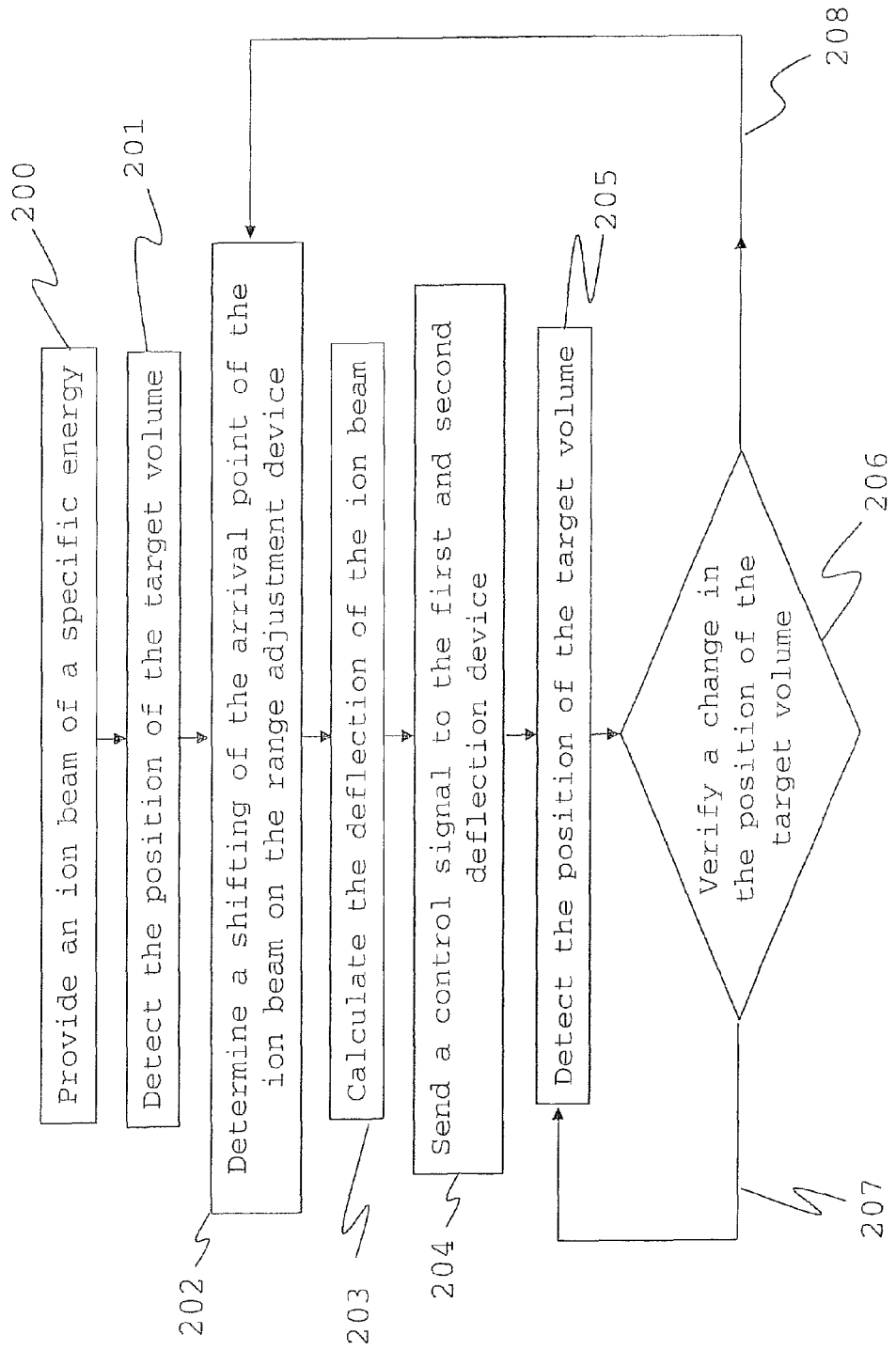

QUICK REGULATION OF THE RANGE OF HIGH-ENERGY ION BEAMS FOR PRECISION IRRADIATION OF MOVING TARGET VOLUMES

DESCRIPTION OF THE INVENTION

The invention concerns a device and a process for adjusting the range of an ion beam, in particular for therapeutic irradiation.

BACKGROUND OF THE INVENTION

In the framework of the pilot project "Tumor therapy with heavy ions," the "Gesellschaft für Schwerionenforschung" [Society for Heavy Ion Research] has irradiated cancer patients having localized tumors in the cranial, neck and pelvic regions since 1997 with carbon ions ranging in energy from 80-430 MeV/u.

The intensity controlled raster scan method, whereby a fine ion beam is conducted in layers over the target volume in a grid array pattern, enables a highly conformal—i.e. adapted to the shape of the tumor—and highly effective irradiation of tumors which are located at some depth in the tissue, while simultaneously protecting the healthy tissue in the vicinity.

A precise, 3-D application dose, however, can only be obtained with a constant predetermined kinetic energy level of the ion beam if the position of the target volume does not change over time. The target volume is frequently referred to as the "clinical target volume (CTV)". In the cranial region, this can be obtained by immobilizing the head using cranial masks which have been individually fitted. For internal organs however, which, for example, may move during respiration, such as the lungs or organs in the thoracic region, this is not possible. As an example, a movement of the target volume in the chest region is particularly problematic because the target volume may be moved within the "shadow region" of a rib.

The present invention concerns itself with the adjustment of the penetration or range of the ion beam, i.e. the position of the Bragg peak in the irradiated tissue, preferably in a moving target volume. While a lateral shifting, from the perspective of the radiation, of the target volume can be compensated for by a quick control of raster scan magnets, shifts in the direction of the radiation require a quick adjustment of the specific energy of the ions, and thereby the position of the Bragg peak in the depths of the tissue.

This is obtained using a passive, so-called range modulation. A narrow high energy ion beam, of approximately 50-400 MeV/u, and highly focused energy, such as is produced by a synchrotron or a cyclotron accelerator, will experience a well-defined energy loss when passing through a piece of homogenous material having a thickness d. By varying the thickness d of this passive range modulator, also known as a "range shifter," it is possible to adjust the initial velocity of the ions, and thereby their range in the tissue. The varying of the thickness is obtained through a wedge-shaped, stepped or curved surface structure of the range modulator.

A solution of this sort is already described in the application WO2005/120641, whereby the range modulator therein consists of two wedges which can be slid in opposition to one another. These are mounted on a linear axle driven by an electromotor located directly in front of the patient.

In the present state of technology, the range modulators are generally of a large size, which react insufficiently quickly and are furthermore of a respectively complex mechanical nature resulting in their having costly and production intensive requirements regarding the adjustments to the linear axle drive. In addition, the quick movement of the wedge drives result in significant noise levels, which may be unpleasant for the patient.

Because the range modulators in the present state of technology are also located directly in front of the patient, the ion beams have no precise kinetic energy due to the statically distributed energy loss. Problematically, an expansion of the ion beam as a result of transversal multiple scattering occurs, such that with conventional systems the range modulator must be placed at a minimal distance (typically, approx. 10 cm) from the patient. Furthermore, secondary fragments, such as neutrons, which are generated by nuclear reactions in a range modulator, are not separated from the ion beam, and generate an uncontrolled and undesired additional dose.

GENERAL DESCRIPTION OF THE INVENTION

With this background information, the present invention assumes the task of providing a device and a process for adjusting the range of an ion beam directed on a target volume, in therapeutic irradiation for example, which will at least reduce the disadvantages occurring in the present state of technology.

For this in particular, a quicker adjustment of the range of the ions to the movement of the target volume, in comparison with that of the present state of technology, should be enabled.

This task is resolved by the device for adjusting the range of an ion beam and the process for regulating an ion beam, in particular for therapeutic irradiation, in accordance with the characteristics of the two independent claims. Beneficial embodiments are described in the respective subsidiary claims.

The invention is concerned with a device for adjusting the range of an ion beam, in particular for therapeutic treatment of a patient by using irradiation of a target volume with ions, comprised of:
  a range adjusting device for the ion beam in which the ion beam experiences different energy losses when passing through different regions of the range adjustment device,
  a sensor for detecting (or ascertaining) the position of the target volume, which provides information describing the detected position,
  a regulating (or controlling) device, which receives the information of the sensor and generates a correlated control signal regarding the position of the target volume, and
  an adjustable first deflecting device, which is located in front of the range adjusting device in the axis of the ion beam, for deflecting the ion beam from its original axis, in order that the ion beam may be directed towards different regions of the range adjusting device, whereby the deflection of the ion beam is configured to the control signal such that the ion beam passes through an appropriate region of the range adjusting device in order that the range of the ion beam is in accordance with the position of the target volume and the Bragg peak is shifted to the region of the target volume.

In addition, the present invention relates to a method for regulating (or controlling) an ion beam, in particular for therapeutic irradiation, containing the following steps:
  providing an ion beam
  determining (or establishing) a reference position or initial reference position of a target volume which is to be irradiated, configuration of the range of the ion beam such that said is adjusted to the reference position of the target volume, in order that the Bragg peak lies within the target volume, verification (or detecting) of a change of the reference position resulting from movement of the target volume, deflection of the ion beam from its axis, particularly in relation to a fixed reference point, such that the ion beam is directed to a point or region of a range adjusting device, which is located in the beam path or beam axis in front of the target volume, in order that the ion beam, in passing through the range adjustment device experiences an energy loss at this point or region, which is configured such that the repositioning (or position change) of the target volume is compensated for by the adjustment of the range of the ion beam, in that the Bragg peak is shifted to the region within the target volume.

The device is constructed particularly in order that it is able to execute the process of the invention. The process may be executed specifically by the device of the invention. Both the process of the invention for regulating (or controlling) an ion beam and the device of the invention for adjusting the range of an ion beam are suited for therapeutic irradiation. An additional potential application is the irradiation of a phantom target (e.g. water phantom) for determining and verifying process parameters. A determination and verification of process parameters is executed before and/or after an actual irradiation. For this purpose, the present invention contains a process for determining and/or verifying process parameters. The term ion beam refers to heavy and charged particles, such as protons, carbon ions, oxygen ions and/or other, particularly for therapeutic applications, suitable particles, such as pions, anti-protons or compounds of said particles. The ion beam is deflected prior to the range adjustment by the first deflection device from its original beam axis. Preferably, the ion beam is deflected in only one plane by the first deflection device. In one embodiment, the ion beam is deflected on one axis which runs laterally offset to the beam axis. In another embodiment, the ion beam is deflected to an axis which runs parallel and laterally offset to the beam axis. Preferably, the deflection is achieved using an applied magnetic field generated by the first deflection device.

The ion beam penetrates, due to its altered beam axis, the range adjustment device in different regions. The ion beam experiences different energy losses according to the penetrated region or the point at which the ion beam arrives at the range adjustment device.

Because the ion beam, dependant on the point at which it arrives at the range adjustment device, experiences different energy losses in passing through the range adjustment device, the range adjustment device is also referred to as a position dependant energy loss element. In the present description, the range adjustment device is also referred to as a range modulator.

In order to obtain the different energy losses, or respectively, in order to be able to obtain different ranges of the ion beam or different energies, the range adjustment device of one embodiment has differing thicknesses in at least one dimension perpendicular to the beam axis. As a result, the ion beam is deflected in a plane perpendicular to the beam axis by the first deflection device, such that the ion beam passes through the range adjustment device at different thicknesses.

The energy loss of an ion beam is however not only dependant on the thickness, but also on the material or the density of the range adjustment device. For this reason, in an additional or alternative embodiment, the different energy losses of the ion beam are generated by variations of the material composition of the range adjusting device. For example, individual regions of the range adjustment device, preferably in at least one dimension perpendicular to the beam axis, may be selectively enriched with different materials.

The deflection device directs the ion beam at a specifically desired point of the range adjustment device. Preferably, the ion beam is moved in only one dimension, specifically along a line, across the range adjustment device. Because the ion beam itself is moved across the range adjustment device, an active range adjustment or an active range modulation is achieved. The range adjustment device itself is, however, immobile, and therefore is not moved. An alteration of the beam axis is made relative to a fixed reference point.

The range adjustment device is located, in accordance with the invention, and in contrast to the present state of technology, not directly in front of the target volume. For this reason, for the appropriate focusing of the ion beam, the size of the range adjustment device may be kept small. The range adjustment device has a length transversal to the beam axis of 2-10 cm, and a width of 0.5-5 cm. The length relates to a plane, in which the ion beam is deflected prior to arriving at the range adjustment device. The width is perpendicular to this. In one embodiment, the range adjustment device is a solid body.

In one embodiment, the present invention contains an adjustable (or controllable) second deflection device for deflecting the ion beam. In a preferred version, the second deflection device generates a magnetic field for deflecting the ion beam. The second deflection device is located downstream from the range adjusting device, as seen from the perspective of the beam axis. Using this second deflection device, the beam axis of the ion beam is altered or adjusted after the range has been adjusted, or respectively, after passing the range adjustment device, in order that said ion beam, having an adjusted range, may be directed towards the target volume. Preferably, the ion beam is redirected to its original axis.

The regulating device, which receives the data from the sensor regarding the position of the target volume, generates an additional correlated control signal for the position of the target volume and for the adjusted range of the ion beam. The second deflection device receives said control signal which is correlated to the position of the target volume, for deflecting the ion beam. The deflection of the ion beam by the second deflection device is configured in accordance with the control signal such that the range, or respectively, kinetic energy of the ion beam, which is to be redirected to its original axis, is adjusted to the position, or respectively, depth of the target volume in the body, and the Bragg peak is shifted to within the region of the target volume.

The ion beam is collimated at least once in at least one of the dimensions lateral to the beam axis after the range adjustment and prior to reaching the target volume. For this, a collimator is intended for placement downstream of the second deflection device in beam direction. The collimator effects a limitation (or definition) of the ion beam in at least one dimension perpendicular to the beam axis. Preferably, the limitation is made in the plane in which the previous deflection was made by the first, or respectively, second deflection device.

An impulse filter is formed by the second deflection device and the collimator. This filters out or removes portions of the ion beam which are not appropriate to the range of the ion beam adjusted to the target volume.

A raster scan device for two-dimensional scanning of the ion beam in the plane perpendicular to the beam axis is located in the beam path for alterations to the lateral position of the ion beam, in particular for scanning the target volume.

The raster scan device is located in the beam direction downstream from the collimator. It is preferably approximately 5-6 meters away from the target volume. It is located in an area where no other means for directing radiation are located. As a result, the range adjustment device is also located upstream of the raster scan device in the beam direction.

Provided that the target volume moves, and thereby the position of the target volume is changed, a lateral position change of the target volume can be compensated for by the raster scan device. In combination with the previous descriptions of the adjustment of the ion beam range, a three-dimensional position change of the target volume, particularly in real-time, i.e. during the irradiation process, can be compensated for.

Because a target volume which is to be irradiated exhibits not only a certain lateral dimension, but also depth, even with immobile target volumes a change is required of the lateral position as well as the (spatial) depth in order to capture or scan all regions of the target volume with the appropriate maximal energy deposition, or respectively, damage. For this, a so-called radiation plan is created. The target volume is scanned according to the radiation plan in both the lateral dimension using the raster scan magnets, as well in its (spatial) depth, using the range adjustment device. Provided that the target volume is mobile, the radiation plan is combined with the movement of the target volume, in order that the three-dimensional position change of the target volume, in particular in real-time, is compensated for, and at the same time the target volume can be scanned.

The sensor successively records the position of the target volume during the irradiation, preferably continuously. The data, containing the position of the target volume, is provided to the regulating device. The regulating device adjusts the axis of the ion beam in respect to movement of the target volume and thereby, to a respective position change of the target volume, thus compensating for the position change of the target volume.

Preferably, the regulating device generates a control signal in respect to a change in the position of the target volume resulting from movement, so that the deflection of the ion beam in respect to the control signal is adjusted such that the ion beam passes through an appropriate region of the range adjusting device, in order that the position change of the target volume is compensated for by the adjusted range of the ion beam and the Bragg peak is shifted to within the region of the target volume.

For this, the regulating device contains the means for establishing, in a first step, the range of the ion beam in relationship to the position of the target volume. In addition, it has the means for establishing, in a subsequent step, the range of the ion beam in relation to a impact (impinging) point on the range adjustment device. Furthermore, it has the means for establishing a specific deflection by the first deflection device in order to arrive at said impact point on the range adjusting device.

The control signal or control signals that are received by the first deflection device, or respectively, are received by the first and second deflection devices, contain(s) the data regarding the degree of deflection to the ion beam. The control signal(s) is (are) correlated in this manner to the position of the target volume.

In addition, the present invention is characterized in that the regulating device can adjust the range in real-time, i.e. adjusts to a movement of the target volume, or respectively in that the range adjustment can be executed in real-time. By way of example, the adjustment is executed cyclically, particularly periodically.

The regulating device can be operated at a regulating frequency in a range greater than approx. 10 Hz, preferably greater that approx. 100 Hz, most preferably greater than approx. 1 KHz, or is operable at a regulating frequency of such.

In addition, the present invention is concerned with a facility for therapeutic irradiation with ion radiation, which contains an accelerator for generating the ion beam and the device for adjusting the range of the ion beam described in the preceding.

The present invention will be explained in detail in regard to the following embodiments. For this, the attached illustrations will be referred to. Identical reference numbers in the individual illustrations refer to identical elements.

DESCRIPTION OF THE ILLUSTRATIONS

FIG. 1.a shows an example of the progression of the energy loss of an ion in a solid body as a function of the specific projectile energy.

FIG. 1.b shows an example of the progression of an ion beam in water as a function of the penetration depth.

FIG. 2.a illustrates the principle of the lateral and longitudinal adjustment of an ion beam to the position of the tissue to be irradiated.

FIG. 2.b shows a schematic presentation of an exemplary embodiment of the device in accordance with the invention.

FIG. 3.a shows a detailed view of an exemplary beam path for an exemplary embodiment of the device in accordance with the invention.

FIG. 3.b shows a detailed view of the exemplary range adjustment device shown in FIG. 3.a.

FIG. 4 shows a schematically in a flow chart the regulating circuit for adjusting the range of an ion beam.

DETAILED DESCRIPTION OF THE INVENTION

Cancer patients having localized tumors are irradiated with a high energy ion beam 10, preferably with an ion beam 10 containing carbon ions, in an energy range of 10-600 MeV/u, having a maximal penetration depth of approximately 40 cm in water. The ion beam 10, in passing through the body tissue 25 is slowed by quasi-continuous collisions with atoms and electrons of the body tissue 25 and looses a portion of its kinetic energy, which is deposited in the body tissue 25. The average energy loss per unit of length, or respectively, the energy E deposited over the length x, is described as the energy loss $dE/dx$.

FIG. 1.a schematically shows the exemplary energy loss $dE/dx$ of an ion from the ion beam 10 in a solid body, such as, for example, human tissue 25, as a function of the specific kinetic energy $E_p/m_p$ of the ion. $E_p$ describes the kinetic energy of the ion, and $m_p$ describes the mass of the ion. The entire, or total, energy loss is a combination of the nuclear energy loss $dE/dx_n$ and the electron energy loss $dE/dx_e$. With small projectile velocities or ion velocities $E_p$, the total energy loss is dominated by the nuclear energy loss, with a maximum of approximately 0.2 keV/u. In contrast, the total energy loss at high ion velocities $E_p$ is dominated by the electron energy loss, having a maximum of approximately 0.5 MeV/u, the so-called Bragg peak or Bragg maximum.

By slowing down the kinetic energy is transferred to tissue 25 along the ion beam trajectory or projectile trajectory resulting in damage to the tissue 25. A higher deposited energy per unit or per volume in the tissue results in a higher level of damage. The energy loss and thereby the level of damage to tissue is largest in the area of the Bragg peak.

The purpose of ion radiation therapy is to achieve the maximal amount of damage to the target volume 20, i.e. the tumor, while simultaneously protecting the neighboring healthy tissue. This can be accomplished with the appropriate selection of the range of the ion beam 10, which is directly proportional to the kinetic energy of the ion beam 10. In the following, the principle of ion radiation therapy will be sketched out using FIG. 1.a for an example of a static tumor.

The ion beam 10 is produced with a defined kinetic injection energy. For this, the ion beam 10 could, for example, be produced with a specific kinetic energy $E_p/m_p$ in a range of $1\text{-}5 \times 10^5$ keV/u (100-500 MeV/u). This is higher than the Bragg peak and takes into account, among other things, the position, or respectively, the depth of the tumor 20 in the tissue 25. This energy range is indicated in FIG. 1.a by a horizontal arrow. The ion beam 10 arrives at the surface of the tissue 25 with this injection energy, which corresponds to a penetration depth of 0 cm. The ion beam 10 arrives at the tissue 25, and penetrates the first layers of the tissue 25. The transferred energy per section dE/dx having a value of approximately 5-10 eV/Å, and the thereby damaged tissue 25 has initially a lower value; particularly in comparison to the Bragg peak, it has a lower value by a factor of approximately 20-40.

In penetrating the tissue 25, the ion beam 10 is successively slowed by the interaction with the tissue 25. As a result, the kinetic energy of the ion beam 10 decreases and the energy loss per section dE/dx increases. At an energy for $E_p/m_p$ of $10^4$ keV/u the energy loss dE/dx is approximately 50 eV/Å, and at a lower $E_p/m_p$ of $10^3$ keV/u the energy loss has a higher value of approximately 185 eV/Å (right slope of the Bragg peak). With an ion beam 10, for which the kinetic energy is adjusted in accordance with the position of the target volume, the ion beam 10 is slowed in such a manner that it reaches the necessary energy $E_p/m_p$ of approximately 500 keV/u, and thereby the Bragg peak with an exemplary dE/dx of approximately 210 eV/Å in the target volume 20. With ion radiation therapy, the kinetic energy of the ion beam is selected such that the Bragg peak is reached in the region of the target volume 20, and thereby is within the region of the tumor 20. Because the tumor 20 may be located at different depths, depending on the point of penetration of the ion beam, the initial kinetic energy of the ion beam must be selected with respect to said depth. This is essential in order to obtain maximal damage in the region of the tumor 20. Because the kinetic energy of the ion beam 10 continues to decrease in the region of the tumor 20, the energy transferred to the tissue 25 is quite low, which can clearly be seen in the low energy side of the Bragg peak (left slope) in FIG. 1.a. As a result, only a small amount or, with a full stopping of the ion beam 10 in the tissue 25, no energy is transferred to the tissue 25 behind the target volume 20. In this manner, using a kinetic energy of the ion beam 10 adjusted to the depth of the tumor 20, while at the same time achieving maximal damage to a tumor 20, the neighboring tissue 25, i.e. both the tissue 25 located in front of and behind the tumor 20, is protected (or less effected).

The underlying physical phenomena of ion radiation therapy are already outlined in FIG. 1.a. The actual "application" of ion radiation therapy is illustrated again using FIG. 1.b. In this case, the energy transferred to a tissue 25 is not presented in the form of a single ion as a function of the specific kinetic energy, as it is in FIG. 1.a. Instead, the dose, i.e. the energy transfer from an ion beam 10 and thereby from numerous ions, in a body 25, is presented. The dose is presented as a function of the range, which is identical to the penetration depth, and not, as it is in FIG. 1.a, as a function of the specific kinetic energy.

The specific kinetic energy correlates however to the penetration depth. Put simply: FIG. 1.b describes the dose, which is given as a sum of the transferred energy in a body from the individual ions. The relative dose a standardized dose based on the maximal value of the Bragg peak. In this case, however, the specific kinetic energy of the ions, which is contained therein due to the successive slowing in the body at various penetration depths, is calculated based on this penetration depth. As an example, a penetration depth of 0 cm at the marked region in FIG. 1.a corresponds to the injection energy. In the penetration of the tissue 25, i.e. with increasing penetration depths, the dose transferred to the tissue increases until said reaches the maximum, or the Bragg peak, and then decreases again.

The curve presented in FIG. 1.b of the relative dose as a function of the penetration depth is derived from the phenomenon illustrated in FIG. 1.a, whereby the energy transferred from one ion in a body is dependant on its specific kinetic energy. This, in turn, is dependant on the penetration depth of the ion in the body, as the ion is successively slowed in the body.

For this, FIG. 1.b shows an exemplary progression of one ion beam 10 in a body 25, using, here, as an example, the transferred (or deposited) dose to water, as a major component of tissue, as a function of the depth in the body 25. The depth dose distributions of a $^{12}C$ ion beam with specific energies of 250 MeV/u and 300 MeV/u are presented in comparison. These energies are within the region marked in FIG. 1.a of the injection energy (horizontal arrow). As a comparison, and to show the advantages of ion radiation 10 over photon radiation, the depth dose distribution of photons having an energy of 18 MV is presented in addition. The maximum dose of the photons is slightly below the surface of the body 25. In comparison, the respective maximum dose of the ion radiation 10 is located in the depth of the body 25, or tissue. The photon dose decreases exponentially. In comparison, the ion dose has a relatively sharp maximum, the Bragg peak, and a relatively steep decline or "cut-off" after the peak. In this manner, the maximum dose, i.e. maximum damage, can be placed in a manner which is particularly sharply defined, or respectively, localized in the depth of the tissue. In addition, through a change in the specific energy of the ion beam 10, the position of the Bragg peak may be changed, or adjusted, in regard to its depth. The width of the Bragg peak is the result of the static nature of a multiple scattering process. This results in a nearly Gaussian shaped range distribution. The observed Bragg peak results from the sum of the depth dose distribution of numerous individual particles, or ions. The combination of a sharp single particle dose with a Gaussian shaped range distribution results in the width of the Bragg peak.

The present invention is concerned with the adjustment of the penetration depth or range of the ion beam 10, i.e. the position of the Bragg peak in a moving tissue 25 which is to be irradiated. Whereby, from the perspective of the radiation beam, sideways shifting of the target volume 20 can be compensated for by a quick adjusting of the raster scan magnets 5, shifts along the axis of the radiation require a quick adjustment of the specific energy of the ions 10 and thereby the position of the Bragg peak in the depths of the tissue 25. FIG. 2.a illustrates for this purpose the principle of lateral and longitudinal adjustment of the ion beam 10, or respectively, the Bragg peak, in regard to its position in the tissue or target volume 20 which is to be irradiated. The inserted graphic is the graphic shown in FIG. 1.b. The ion beam 10 is produced (or provided) with a certain specific energy by an accelerator 12, in this case a synchrotron. The longitudinal position of the Bragg peak is configured by an adjustment of the specific energy, in particular in order to adjust for the position or depth of the target volume 20 in tissue and/or for longitudinal scanning of the target volume 20. Using the dipole magnets 5a and 5b, or the raster scan magnets 5a and 5b, the transversal position of the ion beam 10, or respectively, the Bragg peak, is configured, in particular in order to adjust for the transversal position of the target volume 20 and/or for transversal scanning of the target volume 20. A deflection in the horizontal or vertical plane is affected using the raster scan magnets 5a and 5b.

FIG. 2.b shows a schematic presentation of an exemplary embodiment of the device in accordance with the invention. In contrast to the present state of technology, a wedge or a wedge shaped or step shaped range modulator is used as the range modulator 2, which is located within the beam guidance in front of the raster scan magnets 5. The range modulator 2 may also be referred to as an energy loss wedge in accordance with its function. Preferably, the range modulator 2 is not moved. It is spatially fixed, and in this sense static. In the present state of technology, the adjustment of the range is achieved through two wedge-shaped range modulators which can be moved against each other. The ion beam does not move in this case. Instead, the two range modulators are pushed against each other, which however, is a very complex process due to the necessary precision and the large size of the modulators.

The ion beam 10 is provided by an accelerator which is not shown. By example, a synchrotron accelerator is specified. The configuration of the range or the energy modulation, or respectively the range modulation is obtained in that the ion beam 10 is deflected in a plane perpendicular to the ion beam 10 by a first deflection device 1, a quick magnetic deflection unit, from the beam axis 11 such that it passes through the range modulator 2 at points of varying thickness. The ion beam 10 experiences an energy loss by passing through a range modulator 2, whereby the range modulator 2 effects different energy losses at different points in order to specifically configure (or adjust) the range of the ion beam 10 in the patient tissue. The range modulator 2, which is also referred to as a range adjustment device 2 in accordance with the invention, is preferably wedge-shaped in structure. It is of differing thicknesses in the plane through which the ion beam 10 is deflected.

In the beam direction after the range modulator 2, the ion beam 10 is redirected to its original central beam axis 11 using a second deflection device 3, another quick magnetic deflection unit, in order that the ion beam 10, independently of the actual ion velocity, arrives at the predetermined target point in the target volume 20. As illustrated, the ion beam 10 is thereby returned to the original beam axis 11 after the range adjustment has been made, and directed towards the target volume 20. In detail: The ion beam 10 is first deflected from its beam axis 11 before passing through the range modulator 2 in a first step. In a second step, it is deflected to an axis which is laterally displaced, preferably parallel to and laterally displaced from the beam axis 11. In a third step, the ion beam 10 is deflected from this laterally displaced axis to the direction of the original axis 11. In a fourth step, the ion beam is then returned to the original axis 11.

The collimator 4 positioned behind the second deflection device 3 serves to limit (or to define) the beam expansion resulting from angle scattering caused in the range modulator 2. In combination with the second deflection device 3, it forms an impulse filter, which only allows ions of the desired velocity, or respectively, kinetic energy to pass. From a safety perspective, this enables a precise filtering of the desired kinetic energy. The previously mentioned raster scan magnets 5, of which there are two magnets, are located in the beam direction after the collimator 4 and the ion beam 10 can be directed in an XY plane perpendicular to the beam axis 11 through the target volume 20 with a corresponding lateral displacement.

The body or tissue 25, in which the target volume 20 is located, is schematically represented by the broken lines. A sensor 6, preferably a movement sensor 6, is located in the region of the target volume 20 which records the position and/or a movement of the target volume 20. The movement sensor 6 corresponds to the present state of technology. Examples are an Anzai belt, a video system or probes implanted in the tissue.

The position of the target volume 20 may change along the beam axis as well as sideways to the beam axis 11 through a movement, such as resulting from breathing, of the lungs or soft tissue of a patient, in such a manner that the Bragg peak may be displaced from the target volume 20, and the point at which maximum damage occurs is now possibly located in healthy tissue of the body 25, and no longer in the center of the tumor 20. This is illustrated using the three positions 21, 22, 23 of the target volume 20. This requires both a rapid correction of the lateral position of the ion beam 10 as well as a rapid adjustment of the kinetic energy of the ion beam 10, and thereby the penetration depth.

Sideways shifting of the target volume 20, in relation to the beam axis 11, can be compensated for by a quick adjusting of the raster scan magnets 5. Shifts in the direction of beam axis require however a compensation by a quick adjustment of the specific energy of the ions 10 and thereby the position of the Bragg peak in the depths of the tissue.

In order to obtain a quick adjustment of the range of the ion beam, also referred to as the ion range, the movement of the target volume 20 is detected, preferably time-resolved, by the movement sensor 6. Data 30 regarding the position of the target volume 20, such as a measured value, are sent to a regulating device 7. From the change in the measured value, or respectively, the position change, the regulating device calculates the necessary changes of the ion range and sends an appropriate correction signal 31 to the first deflection device 1 and an appropriate correction signal 32 to the second deflection device 3.

The correction, or control, signal 31 is correlated with the actual position, or respectively, depth of the target volume 20 such that the ion beam 10 is deflected from the beam axis 11 to the appropriate region of the range modulator 2, in order that the energy loss in the range modulator 2 may be adjusted for the depth location of the target volume 20. The correction, or control, signal 32 is correlated with the actual position, or respectively, depth location of the target volume 20, so that the portion of the ion beam 10, which, after the energy loss in the range modulator 2, contains the necessary range, is redirected to the original beam axis 11.

A decreasing of the range of the ion beam 10 is to be obtained through the range modulator 2 only. As a result, the energy of the ion beam 10, which is produced by the accelerator, is to be adjusted for the maximum depth of the target volume 20. This means that the ion beam 10 is to be provided with a kinetic energy prior to its entrance in the range modulator 2, which is sufficient for reaching the maximum depth of the target volume 20, in this case the position 21, or to be able to penetrate even deeper into the body 25. Positions less deep, in this case the positions 22 and 23 of the target volume 20, may be obtained through an energy, or respectively, depth adjustment by the range modulator 2. The shifting of the Bragg peak in the target volume 20 is illustrated by the graphic 24, which shows the energy loss, or respectively, the dose in relation to the depth, or respectively, the penetration depth. The maximum dose is, in each case, adjusted in real-time to the actual position 21, 22, 23 of the target volume 20, i.e. adjusted to a movement of the target volume 20. The range adjustment in accordance with the invention may also be used with larger (or extended) static target volumes 20, in order that the target volume 20 may be irradiated at different depths in layers.

An advantage of the embodiment described can be found in the fact that the variation of the thickness of the range modulator 2 is not achieved mechanically, but instead is obtained through the configuration of the magnetic fields, or respectively, the magnetic currents. This enables a range adjustment to be made with greater speed, or respectively, regulating frequency than that obtained using mechanical shifting.

In addition, the range modulator, in contrast to the present state of technology, is not located directly in front of the patient, or respectively, target volume 20. It is located instead upstream in the beam pathway, prior to the raster scan magnets 5. Since the ion beam 10 can be well focused prior to the first deflection device 1, e.g. with a beam diameter of approximately 5 mm, the size of the range modulator 2 can be kept to a minimum. In one embodiment, the range modulator 2 is approximately 6 cm long and 1 cm wide. In contrast to this, a wedge system for modulation which is placed directly in front of the patient, in accordance with the present state of technology, must cover the entire size of the radiation field of approximately 20×20 cm$^2$. This, in turn, results in a significant size, or respectively, mass of the wedges, and a correspondingly high demand on the linear axes drive. In addition, the quick movement of the conventional wedge-drive results in considerable noise levels, which may be unpleasant for the patient. The disadvantages listed are avoided with the invention.

Furthermore, secondary fragments, particularly neutrons, resulting from nuclear reactions in a range modulator 2 may be generated with a construction in accordance with the present state of technology, and not be separated from the ion beam 10, if the range modulator, in the present state of technology, is located directly in front of the patient. Due to the strongly forwards directed angle distribution of the fragments, said particles travel directly into the patient and generate an uncontrolled, undesired, and additional, dose.

FIG. 3.a shows a detailed view of an exemplary guidance of the ion beam 10 (or beam transport system) in an embodiment of the present invention. The ion beam 10 is prepared and runs along the axis 11 into the beam guidance. In particular for guiding and focusing the ion beam 10, the quadrupole magnets 101 and 102 are located in front of the energy loss wedge 2 in beam direction. The ion beam 10 is deflected from its original axis 11 to an axis 11a, which is inclined (or oblique) to the original axis 11, by the first deflection device 1, in this case shown as a horizontal dipole 103. The energy loss wedge 2 is located on this axis 11a. Dependant on the applied strength of the preferably magnetic field of the first deflection device 1, in particular at a constant specific energy of the ion beam 10, the ion beam is deflected to different axes 11a, 11b, 11c, and thereby, in particular, to different points on the energy loss wedge 2. In this case, the ion beam 10 is deflected to the axes 11a, 11b, 11c, which are for essentially parallel and laterally displaced to each other.

Prior to arriving at the energy loss wedge 2, the ion beam 10 passes through a quadrupole magnet 104, specifically for beam guidance and/or shaping, a particularly horizontal steering magnet 105, a particularly vertical steering magnet 106 and an additional quadrupole magnet 107. Preferably, the four components 104, 105, 106, and 107 are arranged in this order following the direction of the beam.

The ion beam 10 arrives at the energy loss wedge 2. Dependant on its axis 11a, 11b, 11c, the ion beam 10 arrives at the energy loss wedge 2 at different points, and passes through said in different regions. The energy loss wedge 2 has different thicknesses in its dimension perpendicular to the beam axis 11a, in this case the width h. In this manner, the ion beam experiences a different, or respectively, defined energy loss dependant on the point at which it arrives at the energy loss wedge 2. The energy loss wedge 2 is, by way of example, located in a vacuum chamber 108. The energy loss wedge 2 is preferably constructed as a trapezoid shaped energy loss wedge 109. It shall be described in detail using the FIG. 3.b in the following.

After passing through the energy loss wedge 2, the ion beam passes through a quadrupole magnet 110, specifically for beam guidance and/or beam shaping, a particularly horizontal steering magnet 111, a particularly vertical steering magnet 112, and an additional quadrupole magnet 113. Preferably, the four components 110, 111, 112, 113 are arranged in this order following the direction of the beam. The four components, 104, 105, 106, and 107, and the four components 110, 111, 112, and 113 can also be arranged basically in mirror symmetry to the energy loss wedge 2.

The ion beam 10 can be deflected by the second deflection device 3, preferably constructed as a horizontal dipole 114, from the axis 11a, 11b, 11c, to the axis 11, which is inclined (or oblique) to the axis 11a, 11b, 11c. Preferably, the raster scan magnets 5, or respectively, 5a, and 5b are located on this axis. In this manner, the ion beam 10 is deflected to the raster scan magnets 5, or respectively, 5a and 5b by the, preferably horizontal, dipole 114. The raster scan magnets 5a and 5b are constructed particularly as quadrupole magnets 115 and 116. Preferably, the ion beam 10 is deflected to an axis 11 thereby, which runs parallel and in particular, laterally displaced to the original axis 11, on which the ion beam 10 arrives at the first deflection device 1.

The single components of the beam guidance are listed in table 1 again, for an overview.

FIG. 3.b shows a detailed view of the energy loss wedge presented in FIG. 3.a. The energy loss wedge is, as an example, constructed in the form of an, preferably, isosceles trapezoid 108. The trapezoid shaped energy loss wedge 108 has a height h, and bases $d_{max}$ and $d_{min}$. The height h describes the width of the wedge, preferably in the horizontal plane. The axis, or respectively, the height h of the energy loss wedge 2 or the trapezoid is perpendicular to the beam axis 11. The length $d_{max}$ describes the maximum thickness of the wedge 2. Should the length $d_{min}$ have a value of zero, or close to zero, the trapezoid 108 thus presented is preferably an isosceles triangle.

The ion beam 10 is provided as a $^{12}$C beam with the energy E. If the ion beam 10 is deflected to the upper axis 11b, the ion beam 10 passes through the energy loss wedge 2 thereby at the upper point, and suffers an energy loss $\Delta E1$. In this manner, the ion beam 10 has a total energy level E-$\Delta E1$ after passing through the wedge 2. If, however, the ion beam 10 is deflected to the lower axis 11b, the ion beams passes through the energy loss wedge at the lower point, and suffers, due to the lesser thickness of the wedge 2 at this point, a smaller energy loss $\Delta E2$. In this manner, the ion beam 10, after passing through the wedge 2 has a higher total energy level E-$\Delta E2$. Should the ion beam 10 pass through the energy loss wedge 2 at some point between these two, for example along the axis 11a, it experiences an energy loss which is larger than $\Delta E2$ and smaller than $\Delta E1$. In this manner, by varying the point at which the ion beam 10 passes through the wedge 2, the energy loss in the wedge 2 and thereby the resulting energy after passing through the wedge 2 of the ion beam 10 can be adjusted to a specific value.

TABLE 1

| Reference no. | Term | Characteristics |
|---|---|---|
| 101 | Quadrupole magnet | $1^{st}$ doublet, $1^{st}$ lens, l = 1,000 mm, $\Delta x$ = 60 mm, $\Delta y$ = 60 mm |
| 102 | Quadrupole magnet | $1^{st}$ doublet, $2^{nd}$ lens, l = 1,000 mm, $\Delta x$ = 60 mm, $\Delta y$ = 60 mm |
| 103 | Horizontal dipole | $\Delta\phi$ = −14.5°, $\rho$ = 6.24998 m, l = 1582 mm, $\Delta x$ = 75 mm, $\Delta y$ = 75 mm |
| 104 | Quadrupole magnet | $2^{nd}$ doublet, $1^{st}$ lens, l = 1,000 mm, $\Delta x$ = 60 mm, $\Delta y$ = 60 mm |
| 105 | Horizontal steering magnet | l = 200 mm, $\Delta x$ = 60 mm, $\Delta y$ = 60 mm |
| 106 | Vertical steering magnet | l = 200 mm, $\Delta x$ = 60 mm, $\Delta y$ = 60 mm |
| 107 | Quadrupole magnet | $2^{nd}$ doublet, $2^{nd}$ lens, l = 1,000 mm, $\Delta x$ = 60 mm, $\Delta y$ = 60 mm |
| 108 | Vacuum chamber with wedge | |
| 109 | Wedge (or "energy degrader") | e.g. $AlMg_3$, $\rho$ = 2.8 g/cm³, $d_{min}$ = 0 mm, $d_{max}$ = 25 mm, h = 70 mm, $\Delta E_{max}$ ≈ 95MeV/u |
| 110 | Quadrupole magnet | $3^{rd}$ doublet, $1^{st}$ lens, l = 1,000 mm, $\Delta x$ = 60 mm, $\Delta y$ = 60 mm |
| 111 | Horizontal steering magnet | l = 200 mm, $\Delta x$ = 60 mm, $\Delta y$ = 60 mm |
| 112 | Vertical steering magnet | l = 200 mm, $\Delta x$ = 60 mm, $\Delta y$ = 60 mm |
| 113 | Quadrupole magnet | $3^{rd}$ doublet, $2^{nd}$ lens, l = 1,000 mm, $\Delta x$ = 60 mm, $\Delta y$ = 60 mm |
| 114 | Horizontal dipole | $\Delta\phi$ = −14.5°, $\rho$ = 6.24998 m, l = 1582 mm, $\Delta x$ = 75 mm, $\Delta y$ = 75 mm |
| 115 | Quadrupole magnet | $4^{th}$ doublet, $1^{st}$ lens, l = 1,000 mm, $\Delta x$ = 60 mm, $\Delta y$ = 60 mm |
| 116 | Quadrupole magnet | $4^{th}$ doublet, $2^{nd}$ lens, l = 1,000 mm, $\Delta x$ = 60 mm, $\Delta y$ = 60 mm |

The parameters used in table 1 are explained as follows: The parameter l describes the effective length of the element, $\Delta x$ is the horizontal aperture of the element (inner radius of the aperture), $\Delta y$ is the vertical aperture of the element (inner radius of the aperture), $\Delta\phi$ is the nominal deflection angle, $\rho$ is the nominal radius of the dipole or the thickness of the wedge, $d_{min}$ is the minimal thickness of the wedge, $d_{max}$ is the maximal thickness of the wedge, and h is the width of the wedge (horizontal plane).

FIG. 4 shows in a flow chart the regulation circuit for adjusting the range and the placement of the Bragg peak of the ion beam 10 in tissue 25. First, in a first step 200, an ion beam 10 is produced having a certain energy. The energy is adjusted to the position or depth of the target volume 20. The energy is at least equal to the energy, or larger than the energy, which is required in order to reach the maximal depth or, in the case of movement of the target volume 20, which corresponds, for example, to the position 21 in FIG. 2.b. In the step 201, the position 21, 22, 23 of the target volume 20 is recorded (or detected). In a next step 202, the shifting of the impact point on the range adjustment device 2 is determined. When the ion beam 10 arrives at this point on the range adjustment device 2, it experiences the corresponding energy loss in passing through the range adjustment device 2, and in this manner the range of the ion beam 10 is adjusted to the depth of the target volume 20. In a subsequent step 203, the deflection of the ion beam 10 is calculated, or determined, which is required in order that the ion beam 10 arrives at the previously determined point on the range adjustment device 2. One of the deflection control signals 31, 32 is sent in the step 204 to the first, or respectively, second deflection device 1, or respectively, 3. After passing through the first deflection device 1, the range adjustment device 2 and the second deflection device 3, the ion beam 10 has the range adjusted for the depth of the target volume. In a next step 205, the position of the target volume is ascertained (or detected) again. In a query 206, it is determined if a position change of the target volume 20 has occurred. Should there be no position change, the process returns in a loop 207 to the preceding step 206, and the position of the target volume is determined or ascertained again. If, however, a position change has occurred, the process returns in a loop 208 to the earlier step 202. The steps 202-208 are repeated and the range of the ion beam 10 is adjusted in real-time to the movement 21, 22, 23 of the target volume 20 within the body tissue 25. The steps 202-208 are repeated during the irradiation continuously.

It is clear to the expert that the preceding described design versions are to be understood as examples. The invention is not limited to these, but rather, can be varied in numerous manners without compromising the essence of the invention.

LIST OF REFERENCE NUMBERS

1 First deflection device
2 Range adjustment device or range modulator or energy loss wedge or wedge
3 Second deflection device
4 Collimator
5 Raster scan magnets
5a Raster scan magnets for deflection in a horizontal plane
5b Raster scan magnets for deflection in a vertical plane
6 Sensor or movement sensor
7 Regulating device (or control device)
10 Ion beam
11 Beam axis
11a Beam axis
11b Beam axis
11c Beam axis
12 Accelerator
20 Target volume or tumor
21 First position of the target volume
22 Second position of the target volume
23 Third position of the target volume
24 Graphic
25 Body or Body tissue
30 Position data
31 Control signal or correction signal for the first deflection device
32 Control signal or correction signal for the second deflection device
101 Quadrupole magnet
102 Quadrupole magnet
103 Horizontal dipole
104 Quadrupole magnet
105 Horizontal steering magnet
106 Vertical steering magnet
107 Quadrupole magnet
108 Vacuum chamber with wedge
109 Wedge (or "energy degrader")
110 Quadrupole magnet
111 Horizontal steering magnet
112 Vertical steering magnet
113 Quadrupole magnet
114 Horizontal dipole
115 Quadrupole magnet
116 Quadrupole magnet
200-208 Process steps in the regulation circuit

The invention claimed is:

1. A device for adjusting the range of an ion beam (10), in particular for the therapeutic treatment of a patient using radiation of a target volume (20) by ions, containing:
a range adjustment device (2, 109) for the ion beam (10) along an original beam axis (11), in which the ion beam (10) experiences different energy losses in the process of passing through different regions of the range adjustment device (2, 109),
a sensor (6) for detecting a position (21, 22, 23) of the target volume (20), which provides data (30) corresponding to the position (21, 22, 23),
a regulating device (7), which receives the data (30) of the sensor (6) and generates a control signal (31) correlating to the position (21, 22, 23) of the target volume (20), and
an adjustable first deflection device (1, 103), which is located prior to the range adjustment device (2, 109) in the direction of the beam, for deflecting the ion beam (10) from its original beam axis (11) to a beam axis (11a, 11b, 11c) that is inclined to the original beam axis (11), in order that the ion beam (10) may be deflected towards different regions of the range adjustment device (2, 109) wherein the range adjustment device (2, 109) is located on the inclined beam axis (11a, 11b, 11c), and wherein the deflection of the ion beam (10) in regard to the control signal (30) is configured such that the ion beam (10) may pass through an appropriate region of the range adjustment device (2, 109), such that the range of the ion beam (10) is adjusted to the position (21, 22, 23) of the target volume (20) and the Bragg peak is placed within the region of the target volume (20).

2. A device in accordance with claim 1, characterized in that
there is an adjustable second device (3, 114) for deflecting the ion beam (10), which is located downstream of the range adjustment device (2, 109) in the direction of the beam, such that the ion beam (10) may be deflected from the inclined beam axis (11a, 11b, 11c) onto a beam axis (11) that is inclined to the inclined beam axis (11a, 11b, 11c).

3. A device in accordance with any of the preceding claims claim 2, characterized in that
the inclined beam axis (11), onto which the ion beam (10) is deflected by the second device (3, 114) for deflecting the ion beam (10), is parallel to and laterally spaced from the original axis (11) on which the ion beam arrives at the first deflection device.

4. A device in accordance with claim 1, characterized in that
the range adjustment device (2, 109) in its dimensions at a right angle to the beam axis (11, 11a, 11b, 11c) has a length of less than 10 cm, and a width of less than 5 cm.

5. A device in accordance with claim 1, characterized in that there is
a collimator (4), which is positioned downstream from the range adjustment device (2, 109) in the direction of the beam, for limiting the ion beam (10) in at least one dimension perpendicular to the beam axis (11).

6. A device in accordance with claim 1, characterized in that
there is a raster scan device (5, 5a, 5b) for two-dimensional scanning of the ion beam (10) in the plane perpendicular to the beam axis (11) for scanning the target volume (20).

7. A device in accordance with claim 6, characterized in that the raster scan device (5, 5a, 5b) is located on the inclined beam axis (11) onto which the ion beam (10) is deflected by means of the second device (3, 114) for deflecting the ion beam (10).

8. A device in accordance with claim 7, characterized in that
there is an impulse filter, which is formed by at least the second deflection device (3) and the collimator (4).

9. A device in accordance with claim 2, characterized in that there is an impulse filter that is formed by at least the second deflection device (3) and the collimator (4).

10. A device in accordance with claim 1, characterized in that
the sensor (6) continuously records the position (21, 22, 23) of the target volume (20) during the irradiation, and the regulating device (7), in regard to a position change of the target volume (20) as a result of movement, re-adjusts the beam axis (11, 11a, 11b, 11c) of the ion beam (10), in order that the position change of the target volume (20) is compensated for.

11. A device in accordance with claim 1, characterized in that
the regulating device (7) executes in real-time the range adjustment for a movement of the target volume (20).

12. A device in accordance with any claim 1, characterized in that
the regulating device (7) can be operated with a regulating frequency in a range which is greater than 10 Hz.

13. A facility for therapeutic radiation with ion beams containing:
an accelerator for generating the ion beam and
the device for adjusting the range of the ion beam (10) in accordance with claim 1.

14. A process for regulating an ion beam (10), in particular for the purpose of therapeutic irradiation, containing the following process steps:
preparation of the ion beam (10) along an original beam axis (11),
determination of a reference position (21, 22, 23) of a target volume (20) which is to be irradiated,
configuration of the range of the ion beam (10) such that said is adjusted for the reference position of the target volume (20), wherein the Bragg peak lies within the region of the target volume (20),
verification of a change in the reference position (21, 22, 23) as a result of movement of the target volume (20),
deflection of the ion beam (10) from its original beam axis (11) to a beam axis (11a, 11b, 11c) that is inclined to the original beam axis (11), in order that the ion beam (10) be directed towards a point on a range adjustment device (2, 109), which is located on the inclined beam axis (11a, 11b, 11c) and upstream of the target volume (20) in the direction of the beam, such that the ion beam (10) experiences an energy loss at this point, which is adjusted such that the position change of the target volume (20) is compensated for by the adjustment of the range of the ion beam (10), in that the Bragg peak is placed in the region of the target volume (20).

15. A process in accordance with claim 14, characterized in that
the range adjustment may be executed in real-time for a movement of the target volume (20, 21, 22, 23).

16. A process in accordance with claim 14, characterized in that
the range adjustment may be operated with a regulating frequency in a range greater than 10 Hz.

17. A process in accordance with claim 14, characterized in that
the ion beam (10) is deflected from the inclined beam axis (11a, 11b, 11c) onto a beam axis (11) that is inclined to the inclined beam axis (11a, 11 b, 11c) after the range adjustment has been executed.

18. A process in accordance with claim 14, characterized in that particles, not exhibiting a range within the adjusted range, may be filtered out of the ion beam (10).

19. A process in accordance with claim 1, characterized in that the ion beam (10), after the range adjustment, and prior to arriving at the target volume (10), at least once, in at least one beam axis (11) is collimated in the lateral dimension.

20. A process in accordance with claim 14, characterized in that the ion beam (10) is deflected onto the beam axis (11) on which the raster scan device (5, 5a, 5b) is located so that the lateral position of the ion beam (10) can be specifically varied in a plane perpendicular to the beam axis.

21. A process in accordance with claim 14, characterized in that the inclined beam axis (11), onto which the ion beam (10) is deflected from the inclined beam axis (11, 11a, 11 b), runs parallel to and laterally spaced from the original axis (11).

* * * * *